United States Patent
Spitzl

(10) Patent No.: US 9,758,444 B2
(45) Date of Patent: Sep. 12, 2017

(54) METHOD AND DEVICE FOR PRODUCTION OF ACETYLENE USING PLASMA TECHNOLOGY

(71) Applicant: Ralf Spitzl, Troisdorf (DE)

(72) Inventor: Ralf Spitzl, Troisdorf (DE)

( * ) Notice: Subject to any disclaimer, the term of this patent is extended or adjusted under 35 U.S.C. 154(b) by 170 days.

(21) Appl. No.: 14/386,959

(22) PCT Filed: Apr. 3, 2013

(86) PCT No.: PCT/EP2013/000983
§ 371 (c)(1),
(2) Date: Sep. 22, 2014

(87) PCT Pub. No.: WO2013/149723
PCT Pub. Date: Oct. 10, 2013

(65) Prior Publication Data
US 2015/0041309 A1    Feb. 12, 2015

(30) Foreign Application Priority Data
Apr. 7, 2012  (DE) ......................... 10 2012 007 230

(51) Int. Cl.
*B01J 19/12* (2006.01)
*C07C 2/76* (2006.01)
*H05H 1/46* (2006.01)
*H01J 37/32* (2006.01)

(52) U.S. Cl.
CPC .............. *C07C 2/76* (2013.01); *B01J 19/126* (2013.01); *H01J 37/32* (2013.01); *H05H 1/46* (2013.01); *B01J 2219/0875* (2013.01); *B01J 2219/1206* (2013.01); *H01J 2237/339* (2013.01); *H05H 2001/4607* (2013.01)

(58) Field of Classification Search
None
See application file for complete search history.

(56) References Cited

U.S. PATENT DOCUMENTS

| | | | | |
|---|---|---|---|---|
| 3,703,460 A | * | 11/1972 | Shair | B01J 19/088 204/170 |
| 4,975,164 A | | 12/1990 | Ravella et al. | |
| 5,273,587 A | * | 12/1993 | Guha | C23C 16/455 118/715 |
| 5,277,773 A | * | 1/1994 | Murphy | C01B 3/24 204/156 |
| 5,695,618 A | | 12/1997 | O'Young et al. | |
| 2006/0163054 A1 | * | 7/2006 | Spitzl | B01D 53/32 204/157.15 |
| 2010/0288494 A1 | * | 11/2010 | Khan | C10G 29/02 166/265 |
| 2011/0190565 A1 | * | 8/2011 | Novoselov | B01J 19/088 585/700 |
| 2014/0183033 A1 | | 7/2014 | Spitzl et al. | |

FOREIGN PATENT DOCUMENTS

| | | |
|---|---|---|
| EP | 0 435 591 A2 | 7/1991 |
| EP | 0 601 798 A | 6/1994 |
| WO | 2004/010454 A2 | 1/2004 |

OTHER PUBLICATIONS

Heintze et al., "Methane conversion into acetylene in a microwave plasma: Optimization of the operating parameters", J. Appl. Phys., vol. 92, No. 5, Sep. 2002, pp. 2276-2283.*
Gruen et al. "Carbon dimer, C2, as a growth species for diamond films from methane/hydrogen/argon microwave plasmas", J, Va. Sci. Technol. A 13 (1995) 1628-1632.*
Hassouni et al. "Investigation of chemical kinetics and energy transfer in a pulsed microwave H2/CH4 plasma", Plasma Sources Sci. Technol. 10 (2001) 61-75.*
International Search Report dated Jun. 14, 2013, mailed Jul. 30, 2013.
English Translation of International Search Report dated Jun. 14, 2013, mailed Jul. 30, 2013.

* cited by examiner

*Primary Examiner* — Kishor Mayekar
(74) *Attorney, Agent, or Firm* — Norris McLaughlin & Marcus P.A.

(57) ABSTRACT

Method and device for the production of acetylene using plasma technology, wherein a gas containing at least one type of hydrocarbon is fed into a non-thermal plasma of a plasma source.

22 Claims, No Drawings

METHOD AND DEVICE FOR PRODUCTION OF ACETYLENE USING PLASMA TECHNOLOGY

This is a 371 of PCT/EP2013/000983, filed Apr. 3, 2013 (international filing date), claiming priority of German Application DE 10 2012 007 230.9, filed Apr. 7, 2012.

The invention relates to a method and device for the production, in particular gas phase production, of acetylene using plasma technology.

BACKGROUND OF THE INVENTION

It has been known to produce acetylene (ethyne, $C_2H_2$) by methods which use arc synthesis. For this, a hot plasma is produced in a hydrogen atmosphere by means of carbon electrodes, via an arc.

Disadvantages of this method are the poor efficiency of typically less than 10%, a low selectivity of the process and the high thermal losses.

It was the object of this invention to overcome these disadvantages and to provide a method and device for the production of acetylene using plasma technology that allows an optimized production of $C_2H_2$.

SUMMARY OF THE INVENTION

This object is achieved by a method in which a gas containing at least one kind of hydrocarbon is passed into a non-thermal plasma of a plasma source.

An advantage of plasma catalysis in the non-thermal or non-equilibrium plasma is the increased efficiency, high selectivity and low thermal losses.

The device comprises a plasma source for generating a non-thermal or non-equilibrium plasma, in particular a plasma source excited by electromagnetic fields, preferably for a plasma excited by microwaves, in the plasma chamber (reaction chamber) of which there is a gas containing at least one kind of hydrocarbon, which is renewed continuously by a feed line. The plasma source itself can be implemented here as a resonant single- or multi-mode plasma source or non-resonant plasma source.

In a preferred embodiment, the device has on the product side (the outlet of the acetylene) a separation unit at which hydrogen is separated from acetylene, especially a palladium tube, for example.

In addition, it is advantageous if the hydrogen which has been separated in this manner is wholly or partly led back into the reaction chamber. Thus, a further preferred embodiment has, in addition to the separation unit, a recirculation returning the separated hydrogen into the reaction chamber.

In this way, the device supplies itself with all or at least a portion of the hydrogen for one of the processes.

When starting the processes, however, a higher proportion of hydrogen or an additional process gas is usually needed to prevent carbon deposits.

Therefore, the device should preferably always have feeds for feeding a process gas into the reaction chamber.

The hydrocarbon-containing gas contains the basic atoms for the production of $C_2H_2$, carbon, and hydrogen. Preferably this gas comprises methane. In a preferred embodiment, the hydrocarbon-containing gas is natural gas or biogas, since it is easy to obtain and relatively inexpensive.

In a preferred embodiment, in addition to the hydrocarbon-containing gas a process gas is added. Preferred process gases contain elements from the group of hydrogen, argon, nitrogen, helium, and neon. Particularly preferably, the process gas contains hydrogen and/or argon. Hydrogen is advantageous in that formation of soot is suppressed.

Argon is advantageous in that the excitation energy (preferably microwaves) needed to maintain the plasma is less than, for example, with hydrogen. By mixtures of these or further gases, it is possible to adjust the energy consumption or the excitation level.

In a preferred embodiment, the process gas comprises a halogen, in particular fluorine or chlorine. Since during the process more saturated and unsaturated hydrocarbons can occur, it is thereby possible to halogenate the said hydrocarbons, in particular to fluorinate or chlorinate them.

The addition of hydrogen via the process gas, especially if methane is used in the hydrocarbon-containing gas, has the advantage that pure methane can lead, inter alia, to the formation of carbon particles in the conversion, which is prevented by the addition of the process gas. This allows an optimized continuous operation.

Depending on the hydrocarbon used in the gas, during the reaction a certain amount of hydrogen is formed automatically, so that in this case it does not necessarily have to be added in a process gas, or only small additional amounts are needed. If hydrogen is formed during the process, it is usually separated from the acetylene only on the product side. It is thus of advantage if the hydrogen proportion of the gas flowing from the reaction chamber is separated from the residual gases and the acetylene, and then fed back into the reaction chamber.

To prevent the deposition of carbon, it is advantageous if an excess of hydrogen in the H/C ratio of greater than 20/1, especially greater than 40/1, preferably greater than 60/1, prevails in the reaction chamber.

The ratio also depends on the hydrocarbon used. An upper limit for the ratio can be set easily when the efficiency of the process is measured. At too high a proportion of hydrogen, the efficiency decreases.

The excess hydrogen can be used in the further course of the process for partial or complete hydrogenation, in particular in the plasma afterglow, using process or plasma heat. This is preferably done by introducing into the reaction chamber a catalyst, preferably platinum or nickel, or a subsequent hydrogenation is carried out, in particular at other pressures. If this should appear necessary, the hydrogenation can even or likewise be carried out in a further plasma catalytic reaction chamber.

By special conditions for the plasma, conversion rates of methane to acetylene in the range of 90% and higher can be achieved.

In a preferred embodiment, a hydrocarbon-containing gas (KG), particularly $CH_4$, and a process gas (P), in particular $H_2$, are fed into a reaction chamber in the ratio (KG:P) of 1:5 to 1:20. The ratio of H/C is thus, in the case of using $CH_4$ and hydrogen, 14/1 to 44/1.

Preferably, in the reaction chamber, there is a pressure of 0.1 mbar to 1 bar, or a positive pressure up to 20 bar and more during the plasma catalysis. Particular preference is given to pressures of 10-300 mbar, preferably 50-200 mbar in particular 50-100 mbar.

The required ratio of the basic substances is pressure dependent. It is therefore advantageous, to control the pressure and/or the ratio of the gases, based on measurements of the reaction and of the end products. For this purpose, the optical emission of the plasma can be used, for example.

In particular when using hydrocarbons other than methane in the hydrocarbon-containing gas, it is advantageous to adjust the quantitative ratios and pressures. The rule is that more hydrogen reduces the yield, and less leads to soot formation. Here, too, in the reaction chamber there should prevail a ratio H/C of more than 10/1, especially greater than 15/1, preferably greater than 20/1.

In a preferred embodiment, the process, in particular the soot formation and/or the efficiency, is monitored. This is preferably done by methods of the group OES (optical emission spectroscopy), GC (gas chromatography) and MS (mass spectrometry).

If it comes to soot formation, then, for example, the background in the OES rises, i.e. a strong yellow/whitish glow is visible in the plasma. Quartz glasses introduced into the reactor become coated, which reduces the transmission of light through them.

The results of the monitoring of the process can then be used to control the ratio of the gases or the pressure in the reaction chamber, wherein at a predetermined pressure there is just one maximum of the acetylene proportion as a function of the ratio of the gases and vice versa (variation of the pressure at a set ratio).

For example, higher pressure in the plasma chamber leads to increased soot formation or formation of higher hydrocarbons, for example C3 and/or C4 species. Thus, if an increased formation of soot is detected by the process monitoring, it is advantageous to decrease the pressure by, for example, increasing the gas discharge or the suction power. However, in this case, too, the proportion of hydrogen can be increased.

In a preferred embodiment, both the soot formation and the acetylene proportion are monitored during the procedure. For a person skilled in the art it is thus easily possible, by changes in the process gas proportion and in the process pressure to adjust optimum process conditions.

In particular, any contact of the plasma with the wall is to be avoided because it reduces conversion significantly and generally causes fouling of the reactor.

An example of a method of the invention is illustrated below:

A preferred method makes use of a microwave plasma source with a power of 0.5 kW and 1 MW, in particular between 3-100 kW, a feed of 10-40 l/min/kW $H_2$ and 2-4 l/min/kW, preferably 3.8 l/min/kW $CH_4$ into a reaction chamber, so that a pressure of 20-300 mbar is present. In this way, a conversion of methane to acetylene of 85-99% can be achieved.

Another preferred method does not require the supply of additional process gases. To avoid a strong formation of soot, here, a much higher amount of gas is passed through the plasma chamber than can be converted by the power coupled in. At a 100% power input into the conversion process, about 1.9 l/min/kW acetylene can be produced from 3.8 l/min/kW methane as a primary gas. If, at a given power, approximately this amount is supplied as a gas, one observes a strong soot formation.

Surprisingly, it turns out that if the gas flow with respect to the calculated value of the theoretical conversion for a given power is more than doubled or even increased tenfold or twentyfold, sooting can be almost completely suppressed, or coating of the plasma region can even be suppressed entirely. In a preferred subsequent step, the acetylene is separated from methane, for example by cooling. The unused methane can then be supplied to the plasma process again. Here a conversion of methane to acetylene of 85-99% can be achieved.

Accordingly, in another preferred embodiment of the process, only the hydrocarbon gas(KG) is introduced into the plasma chamber, wherein the gas flow rate of the hydrocarbon gas exceeds that which can be maximally, theoretically converted by the power coupled in at least by a factor of 2, preferably by a factor of 10 to 20 or higher.

Optionally, the hydrocarbon gas(KG) that has not been converted to acetylene during the first pass is separated from the product gas stream and introduced, in whole or in part, into the plasma chamber.

In the described methods, apart from the hydrocarbon gas, other gases, such as hydrogen, air, oxygen or halogens, and liquids such as water, in particular in the form of aerosols, or solids, such as microparticles or nanoparticles, optionally from catalyst materials, can be admixed. In this way it is possible to control yields and products.

Solids can be separated from the gas stream in the output stream, for example by cyclones, and possibly admixed to the input stream after a treatment or conditioning.

In another preferred embodiment, the plasma gas is cooled downstream of the plasma source, for example by a gas quench cooler or a liquid quench cooler.

And liquid reactants (e.g. higher hydrocarbons or water) can be introduced into the plasma zone, preferably in the form of aerosols. Likewise, it is possible to evaporate them, using the process heat, and then supply them in gaseous form.

The technically preferred microwave frequencies are the frequencies used in industry of 440 MHz, 915 MHz and 2.45 GHz. The methods are not limited to these frequencies. High-frequency excitation (HF, UHF/VHF) is also possible. In some embodiments, the excitation frequency is in the range of 0.1-500 GHz, preferably in the range of 0.3-6 Ghz.

The device of the invention preferably has an internal plasma chamber but also external plasma chambers are suitable. The plasma reactor is flowed through by the gases being used.

The device can be ignited in a low pressure range of up to several 10 mbar and does therefore not require a plasma initiator.

In a preferred embodiment, a flicker protection, preferably at least one bluff body, in particular of cylindrical or conical shape, is introduced into the plasma zone, or an eddy/vortex is generated by a tangential approach flow. This serves to stabilize the plasma zone and is advantageous as an unstable, flickering plasma interferes with the process, increases slip, and can also increase by-products. It is also possible to conduct a part of the gases, for example the hydrocarbon-containing gas, through the bluff body/bluff bodies itself/themselves. As in this way the hydrocarbon is guided through the plasma zone, which is located above the bluff body, a nearly complete excitation of the hydrocarbon can be ensured. The gas can also be supplied via several zones, such as concentric zones, of the bluff body or bluff bodies.

The elements for stabilizing the plasma zone are preferably designed to be moveable or adjustable in order to adapt the flow through the plasma reactor or the plasma region to the respective volume flow rates and gas mixtures.

A bluff body itself is typically made of metal or carbon, in particular graphite. Preferably, it contains a catalyst material or a coating of a catalyst material, especially of platinum or nickel. The lid and the pipes in the afterglow of the plasma can also comprise a catalyst material or a coating of a catalyst material.

In a preferred embodiment, the plasma chamber is designed as a tube section. This has the advantage that the gases have a free frontal access to and/or exit from the plasma chamber.

Also advantageous is a lateral coupling of the microwaves into the plasma chamber (reaction chamber). Coupling of the microwaves by means of several coupling points is advantageous as well since hereby the power transfer per coupling point can be reduced.

All components of the device can also occur multiple times.

The invention claimed is:

1. A process for producing acetylene using plasma technology, wherein a gas containing at least a hydrocarbon and further comprising hydrogen gas is introduced continuously via an inlet into a non-thermal plasma which is present in a reaction chamber of a microwave plasma source, said gas being renewed continuously by a feed line; and said hydrocarbon is at least partially converted to acetylene in said reaction chamber; wherein said acetylene, which is present in a product gas stream flowing from the reaction chamber, is separated from hydrogen which is also present in the product gas stream; and wherein said plasma is excited by microwaves with a microwave power of at least 3 kW.

2. The process according to claim 1, wherein the microwave power is 3 kW to 1 MW.

3. The process according to claim 1, wherein the plasma source is excited with an excitation frequency which is in the range of 0.1-500 GHz.

4. The process according to claim 1, wherein in addition to the hydrocarbon-containing gas, at least one process gas is added which contains elements selected from the group consisting of argon, nitrogen, oxygen, carbon, helium, fluorine, chlorine and neon.

5. The process according to claim 1, wherein the product gas stream flowing from the reaction chamber comprises said acetylene, residual gas and a hydrocarbon proportion which has not been converted to acetylene, and said proportion which has not been converted to acetylene is separated from the product gas stream and then reintroduced completely or partially into the reaction chamber.

6. The process according to claim 1, wherein an excess of hydrogen prevails in the reaction chamber, with an H/C ratio being greater than 10/1.

7. The process according to claim 1, wherein a pressure of 0.1 mbar to 1 bar is present in the reaction chamber.

8. The process according to claim 7, wherein soot formation is monitored and, if an increased formation of soot is detected, the pressure in the reaction chamber is decreased.

9. The process according to claim 8, wherein the soot formation is monitored by OES (optical emission/spectroscopy).

10. The process according to claim 1, wherein an excess of hydrogen to carbon prevails in the reaction chamber, with an H/C ratio being greater than 10/1, and wherein a pressure of 10-300 mbar is present in the reaction chamber.

11. The process according to claim 1, wherein said microwave power is between 3-100 kW, the hydrogen gas is fed at a flow rate of 10-40 l/min/kW and methane as the hydrocarbon is fed at a flow rate of 2-4 l/min/kW to the reaction chamber, and/or a pressure of about 20-300 mbar is maintained in the reaction chamber.

12. The process according to claim 1, wherein the process is monitored by measurement methods selected from the group consisting of OES (optical emission/spectroscopy), GC (gas chromatography) and MS (mass spectrometry).

13. The process according to claim 1, further comprising a subsequent step in which the acetylene which is present in the product gas stream is separated from a methane proportion which has not been converted to acetylene by cooling.

14. The process according to claim 1, wherein the product gas stream flowing from the reaction chamber comprises said acetylene, residual gases and a proportion of hydrogen, and said proportion of hydrogen is separated from the residual gas and the acetylene and is optionally fed back to the reaction chamber.

15. The process according to claim 1, wherein in addition to the hydrocarbon-containing gas, at least one additive selected from the group consisting of liquid reactants and solid materials is added.

16. The process according to claim 15, wherein said solid materials are in the form of microparticles or nanoparticles.

17. The process according to claim 15, wherein said solid materials are wholly or partly comprised of catalyst materials.

18. The process according to claim 15, wherein said liquid or solid additives are separated from the product gas stream and then reintroduced into said non-thermal plasma via said inlet.

19. The process according to claim 1, wherein the plasma is ignited without using a plasma initiator.

20. The process according to claim 1, wherein in addition to the hydrocarbon-containing gas, at least halogen is added to produce halogenated hydrocarbons.

21. The process according to claim 20, wherein said halogen is selected from the group consisting of fluorine and chlorine.

22. A process for producing acetylene from hydrocarbon gas by using plasma technology in a reaction chamber, wherein only the hydrocarbon gas is introduced into the reaction chamber which contains a plasma excited by microwaves at a microwave power of at least 3 kW, the hydrocarbon gas being introduced with a flow rate which is adjusted such that it exceeds a flow rate which is maximally, theoretically converted to acetylene by the microwave power coupled in at least by a factor 2; and a proportion of hydrocarbon gas that has not been converted to acetylene is separated from the product gas stream and reintroduced, in whole or in part, into the reaction chamber.

* * * * *